United States Patent
Gunneskov et al.

[11] Patent Number: 5,970,800
[45] Date of Patent: Oct. 26, 1999

[54] METHOD OF DETERMINING THE MASS FLOW OF A FLOW OF GRAINS

[75] Inventors: Ole Gunneskov, Hadsten; Knud Fabrin, Jyderup, both of Denmark

[73] Assignee: Dronningborg Industries A/S, Randers, Denmark

[21] Appl. No.: 08/952,689

[22] PCT Filed: May 29, 1996

[86] PCT No.: PCT/DK96/00226

§ 371 Date: Apr. 13, 1998

§ 102(e) Date: Apr. 13, 1998

[87] PCT Pub. No.: WO96/38714

PCT Pub. Date: Dec. 5, 1996

[30] Foreign Application Priority Data

Jun. 2, 1995 [DK] Denmark ................... 0631/95
Jan. 23, 1996 [DK] Denmark ................... 0069/96

[51] Int. Cl.[6] .................................................. G01F 1/66
[52] U.S. Cl. ............................................... 73/861.28
[58] Field of Search ..................... 73/861.28, 861.26–18

[56] References Cited

U.S. PATENT DOCUMENTS 1,851,215  3/1932  Schunemann .
4,314,241  2/1982  La Plante et al. .
5,369,369  11/1994  Cutmore .

FOREIGN PATENT DOCUMENTS 126523      7/1973   Denmark .
1 917 571   10/1969  Germany .
24 45 046   4/1976   Germany .
932536      6/1973   U.S.S.R. .
WO 85/00087 1/1985   WIPO .

*Primary Examiner*—Richard Chilcot
*Assistant Examiner*—Jewel Thompson
*Attorney, Agent, or Firm*—Darby & Darby

[57] ABSTRACT

A method of determining the mass flow speed of a granular material through a channel by means of electromagnetic waves, preferably in the microwave area. According to the invention, either the attenuation or the phase-shift is measured or both the attenuation and the phase-shift and optionally also the reflection. Based on the knowledge of both the reflection and the absorption it is possible to determine the type of grains being involved because the proportion of these magnitudes is characteristic of the various types. When measuring especially oil-containing grains which are able to have an effect on the dielectricity constant, it is advantageous to measure the phase of the transmitted signal because the phase-shift is substantially proportional to the flow of such grains.

9 Claims, 5 Drawing Sheets

METHOD OF DETERMINING THE MASS FLOW OF A FLOW OF GRAINS

FIELD OF THE INVENTION

The invention relates to a method of determining the mass flow speed of a granular material through a channel by means of electromagnetic waves, microwaves from a transmitter to a receiver. The invention relates in particular to measurements performed in moving combine harvesters, where it is important to know the quantity of grains conveyed to the grain tank of the combine harvester. The invention is, however, related to the measuring of a grain flow or a material flow in general.

BACKGROUND OF THE INVENTION

Several systems have been suggested for such a measuring of the flow, such as by means of yielding guard plates being pushed more or less backwards in response to the force they are subjected to by an incoming falling flow of the granular material. It has, however, been recognized that such mechanical measuring methods are too uncertain and that it is possible to employ a more advanced measuring technique based on radioactive radiation. Thus it has been found that it is possible to achieve a well-defined expression of the mass flow of a granular material by said flow passing a measuring area, where a radioactive radiation is emitted from one side of said measuring area towards an opposing side where a receiver detects the radiation and continuously detects the amount of radiation absorbed by the grain flow. In this manner it is possible to determine the mass flow.

Although it is thereby possible to employ radioactive sources which are in fact of a neglectable size, the Authorities have declared that such sources should be avoided because they require so much inspection that an inspection of thousands of moving units would be completely unrealistic.

According to the invention it has been recognized that it is possible to use an officially acceptable type of radiation-based mass determination. In other words it is possible to use electromagnetic microwaves in a frequency area where a predetermined quantity of radiation has been allowed. Besides it is by the present invention sufficient to employ a power of the magnitude of 1 W, whereby suitable shieldings may secure that the radiation problems are reduced to an acceptable level.

It is known from U.S. Pat. No. 4,628,830 to perform a continuous determination of the mass flow in a flow of granular material by means of microwaves. However, this publication deals only with absorption of the wave energy caused by the water content in a coal powder fed to a burner in a power station. The measuring is performed on a falling flow of the material in a pipe where a microwave generator is placed opposite a receiver. In this manner it is possible to measure the amount of energy absorbed in the material, or rather to obtain an expression of the variations applying to the mass flow and thereby to calibrate said variations into an expression of the mass flow. A measuring of the water flow is aimed at, where said water flow in a predetermined material represents the flow of the material itself for a predetermined water content.

The above is possible as long as the material in question is almost homogeneous. A fundamental condition applies, however, to combine harvesters, namely, that the measuring device must be able to operate with various types of material which in no way is homogeneous. The major advantage obtained by the use of the above radioactive radiation is indeed that it is possible to operate with a well-defined calibration of the equipment for various types of grains and seeds.

A substantially analogous use of microwaves does not provide a similar result. Tests performed on microwaves of the type being commercially used exactly for emission of energy into wet substances turned out to be extremely unfortunate, for instance in connection with absorption of energy for heating products in microwave ovens, as it turned out to be impossible by means of one and the same equipment to obtain merely tolerably correct measurements of various mass flows of various granular materials.

It has, however, nevertheless become possible by the invention to base the measurings on the use of microwaves. A method of determining the mass flow speed of a granular material, such as grains, through a channel by means of electromagnetic waves, microwaves from a transmitter to a receiver is characterised in that the attenuation and/or the phase-shift for the main signal and optionally the reflection are measured, the amplitude and the phase shift being measured by comparing the main signal through the material with a reference signal of the same frequency, the reference signal being provided by comparing the output of the transmitter with an injection signal, said compared signal being transmitted through a separate connection to the receiver.

The increased frequency, such as 10 GHz compared to 2 to 3 GHz, results in a considerably higher radiation reflection without considerably influencing the radiation absorption in the material. In other words, the attenuation can be predominantly ascribed to the reflection. At the same time the undesired reflection from the walls of the chamber is increased, and under unchanged conditions the latter renders it almost impossible to obtain useful results.

The associated minimizing of the wall reflection can be obtained in several ways optionally in combination. The chamber can be structured so as not exactly to facilitate reflections towards the measuring window, and it can be coated with radiation-absorbing material, such as sheet material of plastics with carbon powder cast therein. A preferred, although rather complicated possibility is to structure the transmitter aerial system in such a way that the radiation is directed sharply towards the measuring window, whereby only a minor amount of primary radiation causes wall reflections. Good results are obtained by means of slot aerials and focusing parabolic reflectors.

Furthermore, it is important to arrange the measuring chamber in a steady environment. Combine harvesters comprise many metal parts moving relative to one another, and as metal is a good conductor for microwaves, such parts can cause disturbances in the measuring field adjacent the measuring chamber. Although the measuring field adjacent the measuring chamber is shielded, the external forces may, however, manifest themselves to such an extent that a high measuring accuracy aimed at is reduced in case significant vibrations apply. It has surprisingly been found that the measuring chamber is most suitably placed on the location where the radioactive measuring system was previously placed.

On this measuring location, namely, at the top of a pipe bending on a grain channel hoop, the radioactive system aimed at an almost homogeneous distribution of the material transverse to the grain flow, and this is another advantageous aspect of the technique using said measuring location according to the invention because this technique also turned out to operate in the best possible manner with a homogeneous distribution of material. The latter would be of no importance or at least far less importance in connection with measurings based on absorption.

A further incentive for increasing the frequency of the microwaves by the invention is that in order to obtain the desired reflection effect from the various types of grains and seeds it is necessary to take into account that some of these products, such as grass seeds, are of such a small grain size that the grain diameter is smaller than the wavelength of ordinary microwaves for heating purposes and for measuring absorption attenuation, respectively. In view thereof it is according to the invention preferred to operate with a frequency of approximately 22 GHz, i.e. approximately 10 times higher than the frequency for ordinary microwaves, and consequently it is additionally obvious that one should concentrate on attenuation measurings based on reflection rather than absorption.

It is, of course, correct that it is impossible to ignore the attenuation caused by an absorption of the microwave energy in the passing material due to the water content thereof. The importance thereof can indeed be weakened by the use of higher frequencies, but the absorption effect is still a significant factor. Accordingly, it has been accepted that for a good measuring accuracy it is advantageous to perform a supplemental determination of the water content in the measuring mass by means of an independent measuring equipment in or close to the measuring site for the mass flow.

BRIEF DESCRIPTION OF THE DRAWINGS

The invention is explained in greater detail below with reference to the accompanying drawings, in which.

DESCRIPTION OF PREFERRED EMBODIMENTS

Figure 1A:
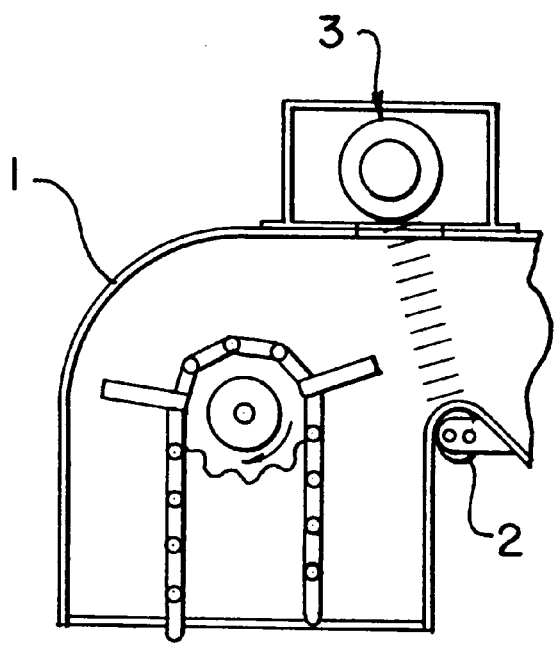
FIG. 1 illustrates the position of the measuring site for the flow measuring.
Figure 1B:
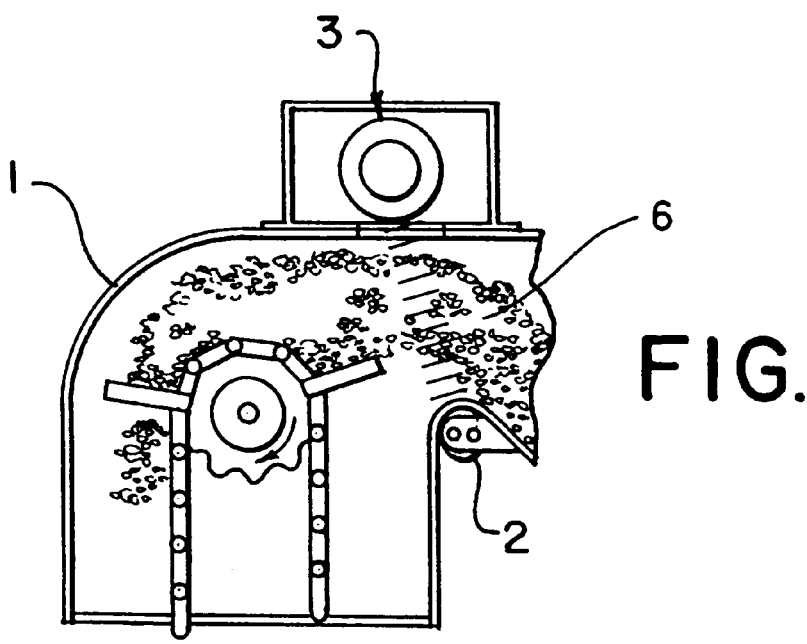

Reference is made to FIGS. 1A and 1B. The measuring site for the flow measuring is advantageously located at the pipe bending 1 on a channel pipe of a square cross section and with a slot-shaped transmitter window 2 of for instance 10 times 80 mm arranged transverse to the pipe in the lower curved pipe wall, as well as a slightly wider, but several times longer receiver window 3 arranged in the upper pipe wall. The windows should be made of a suitable non-absorbing material, such as teflon or a suitable ceramics.

The microwave frequency used can be in a relatively large range, such as 5 to 50 GHz, preferably approximately 20 to 25 GHz. Although the measuring system can be efficiently shielded, and although a power of no more than approximately 1 W is employed, it can be practical to use a frequency released for industrial use, viz. 22.6 GHz, whereby it is easy to observe the official radiation limits.

In principle, it is possible to perform a differential measuring between the transmitted and the received signal strength directly on the high-frequency signals with the result that an expression of the quantity of grains present in the measuring area at the measuring moment can be obtained. A frequent reading of the measuring value, such as every msec. or μsec. renders it possible to determine the flow of grain mass 6 when the advancing speed of said grains is known. The measuring result corresponds to the signal attenuation caused by both the absorption in and the reflection from the grains.

The invention has, however, recognized that it is possible to obtain further information by a further signal processing by means of an amplitude-modulated transmitter signal having a modulation frequency of for instance 100 kHz. The detection of nothing but the modulation frequency can be performed by mixing the transmitter signal before it is modulated with the modulated receiver signal, cf. FIG. 2.

The modulation signal deviates in amplitude as function of the total attenuation caused by the dielectricity constant and the water content of the grains.

The original modulation signal has per se been amplitude-modulated by a frequency depending on the speed of the grains, namely, based on the grain passages through the measuring field, and this superposed modulation is a result of the reflection from the individual grains due to the difference between the dielectricity constants of the grains and the air, respectively. This modulation is called secondary modulation.

This secondary modulation can be measured by detection of the primary modulation signal. The amplitude of the secondary signal is proportional to the reflection of the high-frequency carrier wave. As a result it is possible to determine the reflection when the total transmission loss is known, cf. the measuring of the primary modulation signal. It turned out that the resulting possibility of determining both the reflection and the absorption can be used for determining the type of grain involved because the proportion of these values is characteristic of the various types. Moreover, an advanced signal processing allows the accuracy of the measuring of the grain mass flow to be increased.

While passing the measuring field before and after the central field of said measuring field the grains are advanced along a path diverging from perpendicular relative to said central field. As a result, a Doppler-effect applies which manifests itself in the frequency of the secondary modulation varying by a frequency change Δ proportional to the speed of the grains. As a result, two frequency bands apply with a secondary modulation, namely, the grains are carried into the central field and leave said field. The associated information on the grain speed can be used for verifying the instantaneous speed and consequently for making the measuring of the mass flow very accurate. Otherwise, the speed is set to be proportional to the speed of rotation of the grain conveyor, but fluctuations may apply with various mass distribution, which in unfortunate situations can cause measuring errors.

Figure 2:
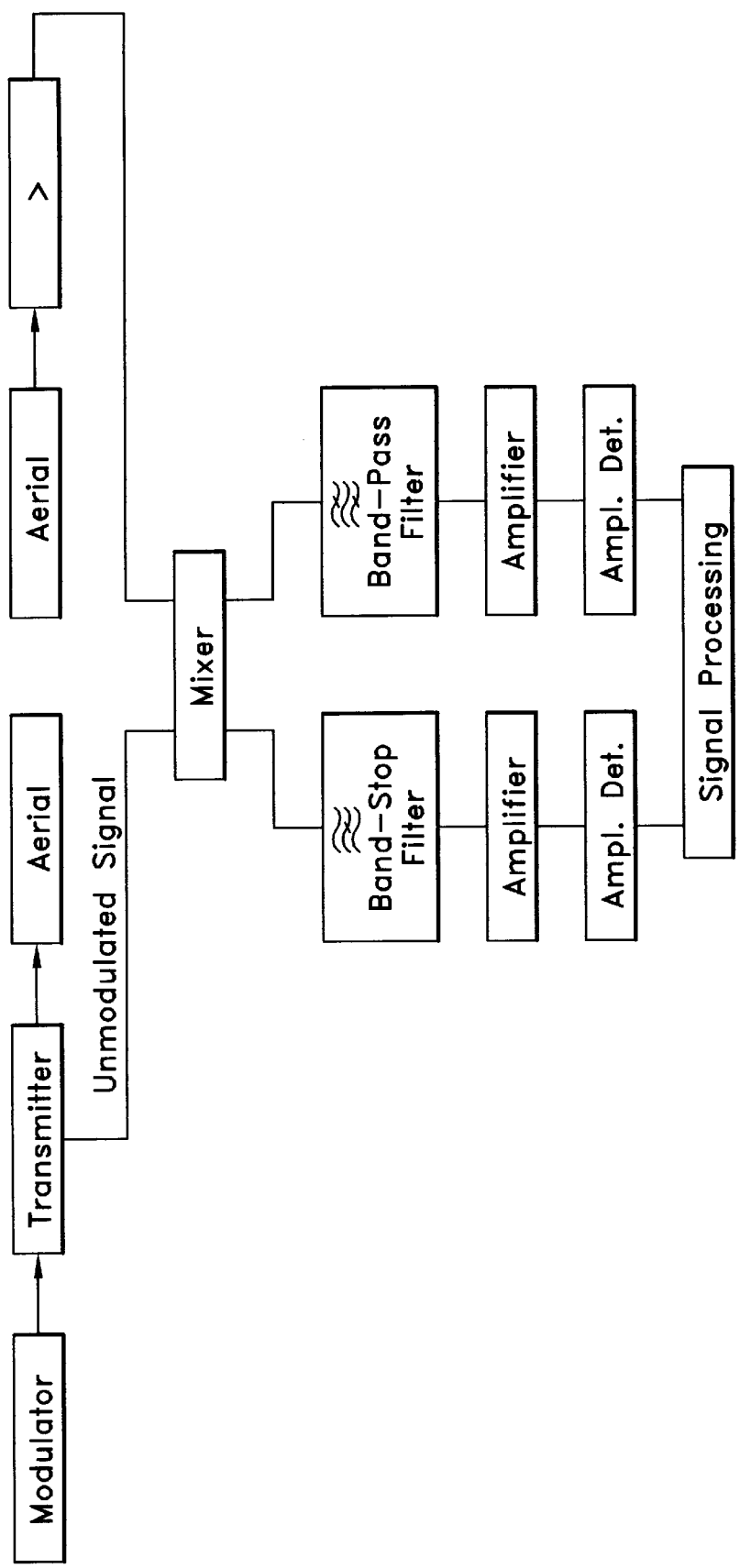
FIG. 2 illustrates an electronic circuit for carrying out the flow measuring and comprising a transmitter and a receiver.

FIG. 2 illustrates the circuit in question. The transmitter is shown which transmits a non-modulated signal to a mixing step. The modulated signal is transmitted through the transmitter aerial, and after passing the grain flow and reaching the receiver aerial said signal is transmitted to said mixing step where it is mixed with the non-modulated transmitter signal. As a result, a signal is transmitted at a frequency corresponding to the modulation frequency through the band-pass filter, and furthermore a signal is transmitted which deviates therefrom by a frequency change Δ (through the band-stop filter) proportional to the speed of the grain. A signal processor provides the attenuation and the speed of the grains, respectively.

It should be mentioned that a further possibility of determining the reflecting radiation applies, namely, to use a cross-polarized receiver aerial or to remove two signals from a cross-polarized receiver aerial, respectively. As a result a signal can be provided which only applies at reflection from the grains. As the reflection depends on the grain size, it is consequently possible to provide information on the type of the grains involved.

As already indicated, the transmitter aerial can be a parabolic aerial focused in one plane so as to meet the demand for operating with a parallel field of a specific size. The receiver aerial can be elliptic focussed on the longitudinal direction of the transmitter aerial. The feeding unit of the receiver aerial is preferably displaced for an optimum utilization of the measuring field.

Figure 3:
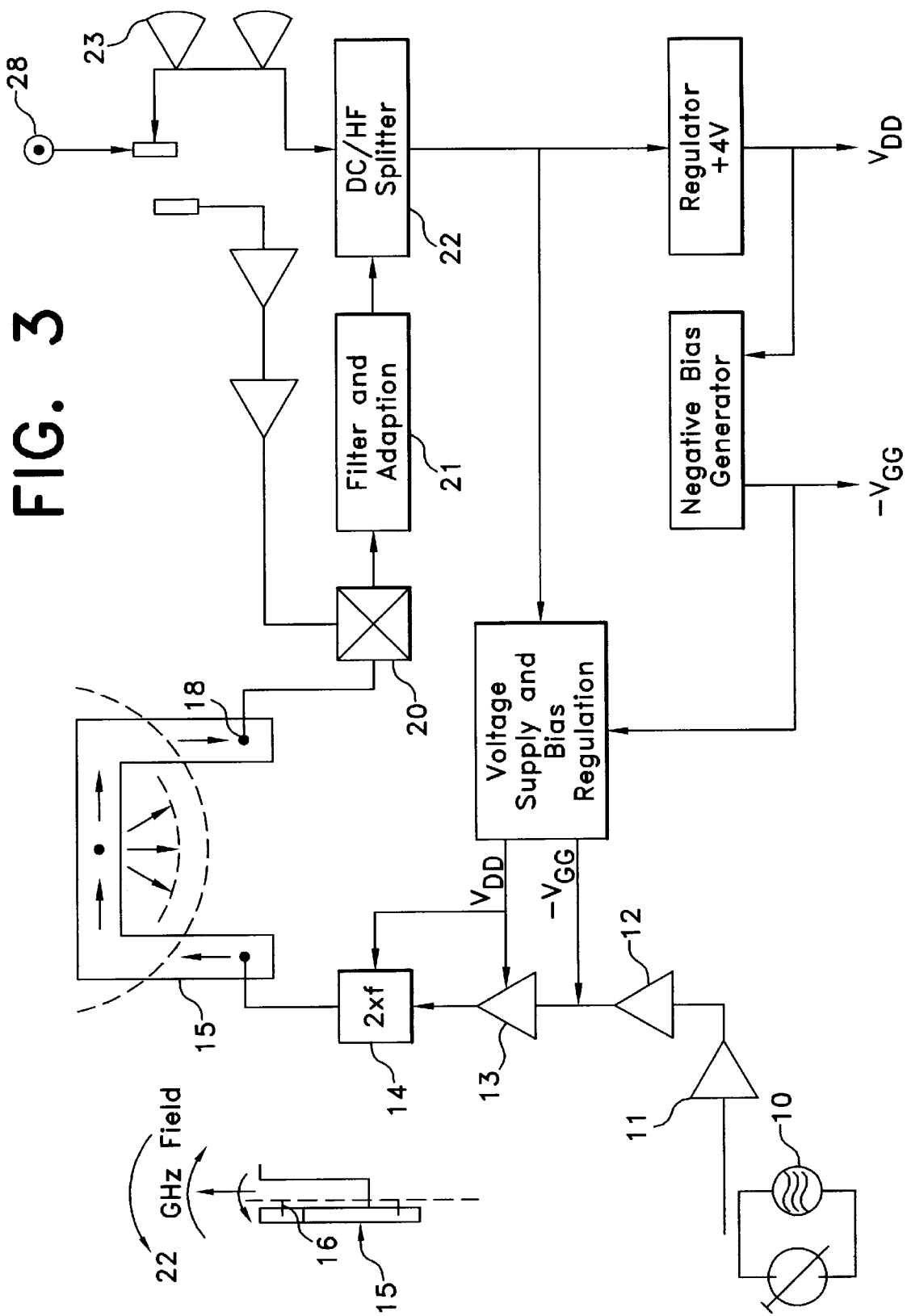
FIG. 3 illustrates the transmitter of the electronic circuit for flow measuring, and which is particularly suited for measuring a flow of oil-containing grains.
Figure 4A:
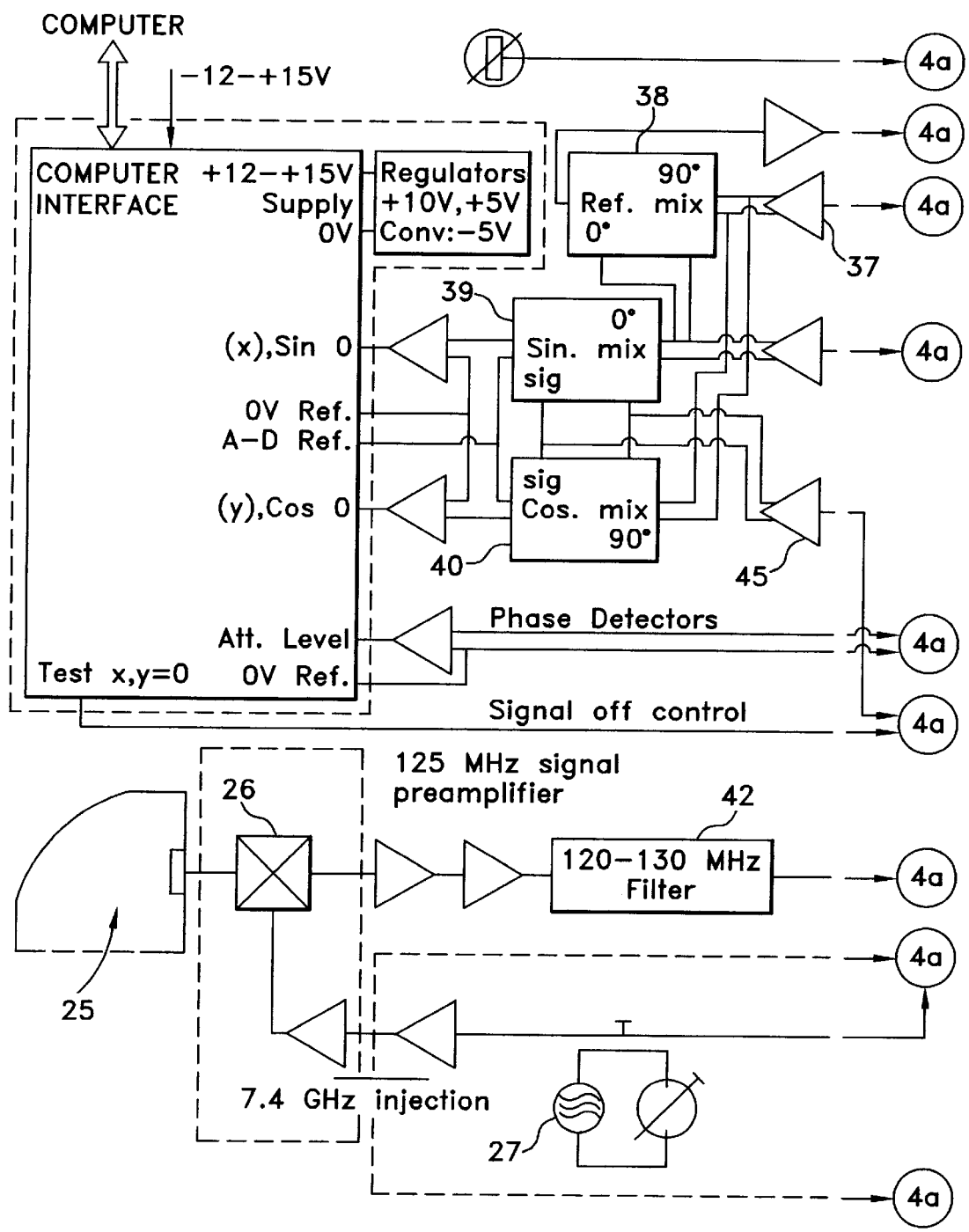
FIGS. 4a and 4b illustrates the receiver mating the transmitter of FIG. 3.
Figure 4B:
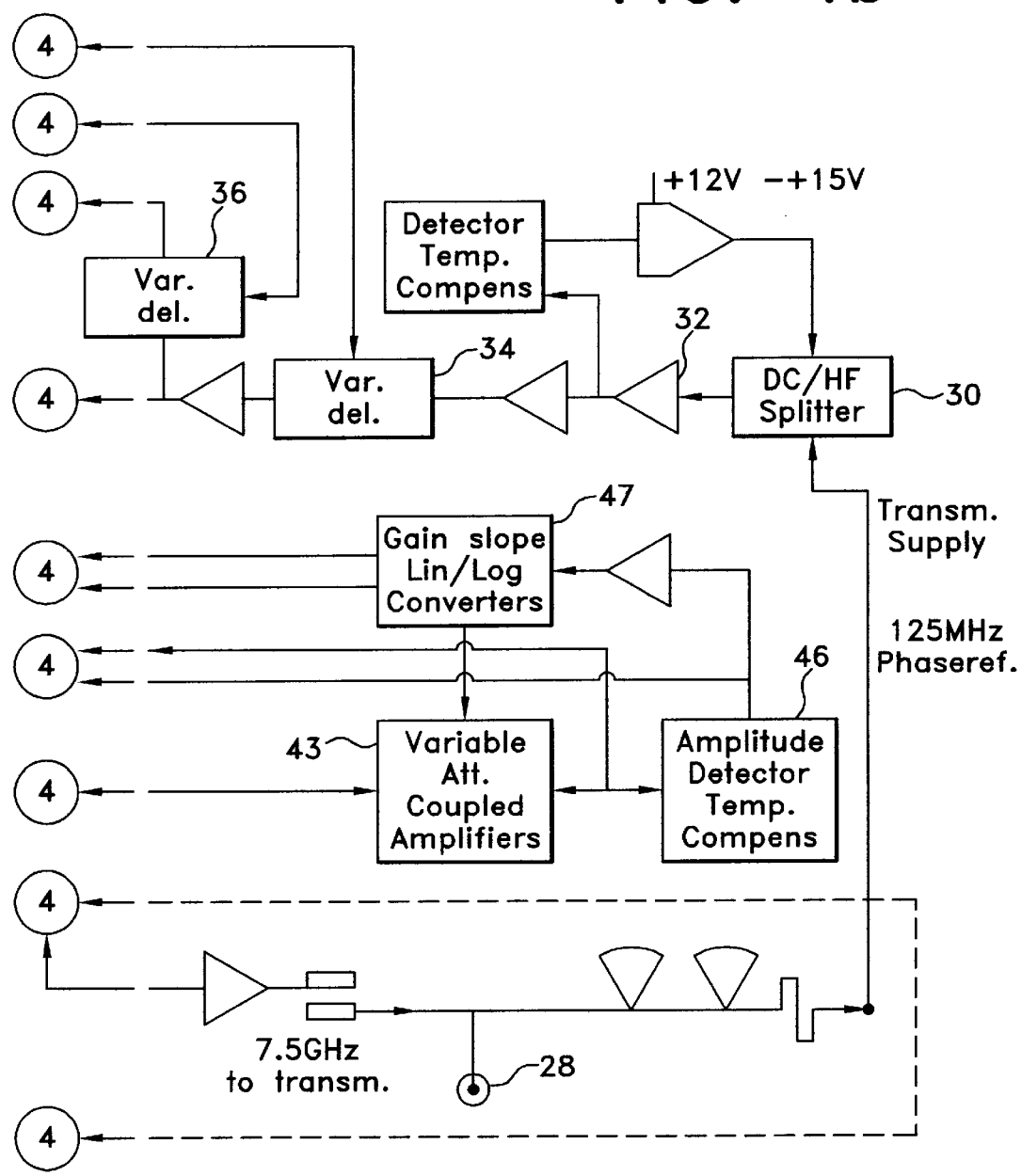

A particularly advantageous embodiment for measuring oil-containing grains, such as rape, is shown in FIGS. 3 and 4. Oil-containing grains influence the dielectricity constant and thereby the phase of the transmitted signal in such a manner that the phase-shift is substantially proportional to the flow of oil-containing grains. However, the attenuation is not influenced in an unambiguous manner, and it cannot be used for measuring the flow.

Like previously, the flow measuring is performed by means of a high-frequency electromagnetic radiation, in this case at a frequency of 22 GHz. A generator 10 transmits a signal of 11 GHz through two amplifiers 11 and 12, a driver 13 and a frequency doubler 14. An adjustment signal is transmitted both to the driver 13 and to the frequency doubler 14 for stabilizing the signal signal amplitude. The frequency-doubled signal of 22 GHz is transmitted to one end of a U-shaped waveguide 15 through a rod-shaped aerial inserted in said waveguide. A small rod-shaped aerial 16 is accommodated in the centre of the U-shaped waveguide 15. The rod-shaped aerial is preferably of a length corresponding to a quarter of a wavelength. At the opposite end of the waveguide 15 a further rod-shaped aerial 18 is provided, said rod-shaped aerial serving as a reference aerial. This aerial 1 8 receives a signal partly being mixed (at 20) with an injection signal of 7.4 GHz from the receiver and used as a reference signal in said receiver and partly being used for running the driver 13 and the frequency doubler 14 (through a filter- and adapting unit 21 and a DC/HF splitter 22). The mixing in the mixing step 20 uses the third harmonic of the injection signal of 7.4 GHz. The mixing step 20 results in a signal of 125 MHz. This signal is transmitted through the filter- and adapting unit 21 to the DC/HF splitter 22. Subsequently, the 125 signal is returned through a filter 23 to the receiver. The signal transfer to the receiver is performed through a semi-stiff cable 28. The 7.4 GHz signal from the receiver is also transmitted through said semi-stiff cable 28. Furthermore, a DC-voltage is transferred from the receiver for running the transmitter. The DC-voltage is fed to a voltage regulator generating the necessary supply voltages.

A chart of the receiver is shown in FIG. 4. The signal transmitted by the aerial 16 of 22 GHz is received at a slot aerial 25. The signal received is mixed in a mixing step 26 with the above injection signal of 7.4 GHz (from 27) after a suitable amplification. The signal of 7.4 GHz is, as previously mentioned, also transmitted to the transmitter through the semi-stiff cable 28. The DC-voltage for running the transmitter is also transmitted through the semi-stiff cable 28. The supply of the DC-voltage is transmitted through a filter. The above reference signal of 125 MHz is also received from the semi-stiff cable 28. This signal is transmitted to a DC/HF-splitter 30 and subsequently to an amplifier 32 and a variable delay 34 (including a varactor diode) for the initial phase setting. The variable delay 34 is set in a specific position. From the variable delay 34 the signal is transmitted to an amplifier and subsequently split into three portions. The first and the second portion is transmitted through a further variable delay 36. Now the signal is transmitted through an amplifier 37 to a phase detector 38 (REFMIX). One of the output signals from the phase detector 38 is returned through a feedback loop to the variable delay 36, which automatically moves to equilibrium position. Moreover, the signal from the amplifier 37 is transmitted to a phase detector 40 (COSMIX). The signal from the variable delay 34 is furthermore transmitted directly to a third phase detector 39 (SINMIX).

Now the main signal is discussed. The signal from the mixing step 26 is a signal of 125 MHz deviating from the previously mentioned reference signal of 125 MHz. The deviations mean that the main signal includes information on the material passed by the signal of 22 GHz. The main signal is transmitted through a filter 42 to a variable attenuator and amplifier 43. The latter amplifier includes a PIN-diode, which in connection with an amplitude circuit ensures that the output signal has a constant amplitude allowing phase comparisons. This output signal is transmitted through an amplifier 45 to SINMIX 39 and COSMIX 40, respectively, and is compared with the reference signal of 125 MHz, whereby a phase is obtained both with respect to the sinus and the cosinus function.

The amplitude circuit comprises an amplitude detector 46 rectifying the signal from the variable attenuator 43. The signal from the amplitude detector 46 is transmitted to a linear logarithmic converter 47, the output signal of which is used as a reference in the variable attenuator 43, which in turn ensures that the output signal has a constant amplitude. This output signal is then the mass flow signal, which by a phase comparison with the reference signal provides both the phase-shift caused by the mass flow and consequently the mass flow.

We claim:

1. A method of determining the mass flow speed of a granular material through a flow channel using electromagnetic waves, such as microwaves, transmitted from a transmitter and received by a receiver, the method comprising the steps of:

providing a main signal of said electromagnetic waves;

transmitting from said transmitter at least part of said main signal to interact with the granular material in said flow channel;

receiving at said receiver an interaction signal corresponding to at least part of the main signal after interaction with said granular material;

providing said receiver with a reference signal; and measuring at least one parameter of the interaction signal selected from the group consisting of amplitude attenuation and phase-shift, by comparing the amplitude and phase, respectively, of said interaction signal with the amplitude and phase, respectively, of the reference signal, wherein said reference signal has substantially the same frequency as said interaction signal.

2. A method according to claim 1 further comprising the step of providing an injection signal, wherein the step of transmitting at least part of said main signal comprises transmitting a first part of said main signal;

wherein the step of receiving said interaction signal comprises the steps of receiving the first part of said main signal after interaction with said granular material and mixing said interaction signal with a second part of said injection signal to provide a mixed interaction signal;

wherein the step of providing said reference signal comprises the step of mixing a second part of the main signal with a first part of said injection signal to provide said reference signal; and wherein the step of measuring at least one parameter of the interaction signal comprises measuring said at least one parameter by comparing the amplitude and phase, respectively, of the mixed interaction signal with the amplitude and phase, respectively, of the reference signal.

3. A method according to claim 1 wherein said interaction with the granular material comprises absorption of said electromagnetic waves by the granular material.

4. A method according to claim 1 wherein said interaction with the granular material comprises reflection of said electromagnetic waves by the granular material.

5. A method according to claim 1 wherein the reference signal is provided to said receiver separately from said interaction signal.

6. A method according to claim 1 further comprising the step of eliminating reflections from the walls of said flow channel by coating the inner surfaces of said walls with a electromagnetic wave-absorbing material.

7. A method according to claim 1 further comprising the steps of: measuring the water content of the granular material; and correcting the mass flow rate measurement based on the measured water content.

8. A method according to claim 1 wherein the receiver comprises a cross-polarized aerial for generating a signal resulting only from reflections from the grains.

9. A method according to claimed claim 1, wherein the receiver comprises an elliptic aerial.

* * * * *